(12) United States Patent
Muyo et al.

(10) Patent No.: US 9,039,183 B2
(45) Date of Patent: May 26, 2015

(54) OPHTHALMOSCOPES

(71) Applicant: Optos PLC, Dunfermline (GB)

(72) Inventors: Gonzalo Muyo, Edinburgh (GB); Derek Swan, Fife (GB)

(73) Assignee: OPTOS PLC, Dunfermline (GB)

( * ) Notice: Subject to any disclaimer, the term of this patent is extended or adjusted under 35 U.S.C. 154(b) by 0 days.

(21) Appl. No.: 14/134,572

(22) Filed: Dec. 19, 2013

(65) Prior Publication Data
US 2014/0185011 A1 Jul. 3, 2014

(30) Foreign Application Priority Data
Dec. 21, 2012 (GB) .................................. 1223180.9

(51) Int. Cl.
A61B 3/00 (2006.01)
A61B 3/12 (2006.01)
A61B 3/14 (2006.01)

(52) U.S. Cl.
CPC ................ *A61B 3/12* (2013.01); *A61B 3/0025* (2013.01); *A61B 3/14* (2013.01)

(58) Field of Classification Search
CPC ....... A61B 3/1005; A61B 3/003; A61B 3/117
USPC ......................................... 351/206, 205, 246
See application file for complete search history.

(56) References Cited

U.S. PATENT DOCUMENTS 5,106,183 A 4/1992 Yoder, Jr.
2008/0204656 A1 8/2008 Fujita et al.
2014/0327877 A1* 11/2014 Hemert et al. ................ 351/206

FOREIGN PATENT DOCUMENTS

WO WO-2009/056161 5/2009
WO WO-2012/162599 11/2012

OTHER PUBLICATIONS

EP Search Report for EP Application No. 13275317.9 dated Mar. 27, 2014.

* cited by examiner

*Primary Examiner* — Hung Dang
(74) *Attorney, Agent, or Firm* — Christopher J. McKenna; Paul M. H. Pua; Foley & Lardner LLP

(57) ABSTRACT

This disclosure is directed to systems and methods for determining a correction for distortion in eye representations of an ophthalmoscope. A digital model of an optical system including the ophthalmoscope and a model eye may be constructed. The digital model may be transmitted to a ray tracing system. A ray may be passed through the optical system onto a surface of the model eye. A measurement of the ray at the surface of the model eye, with distortion, may be calculated and an angular position of a horizontal scanning element and an angular position of a vertical scanning element can be determined. Using the horizontal scanning angle and vertical scanning angle, a measurement of the ray at the surface of the model eye, without distortion, may be calculated and compared to the measurement with distortion to determine a correction for distortion in eye representations of the ophthalmoscope.

18 Claims, 3 Drawing Sheets

OPHTHALMOSCOPES

RELATED APPLICATION

The present application claims priority to UK Application No 1223180.9 filed on Dec. 21, 2012, which is incorporated herein by reference in its entirety for all purposes.

FIELD OF DISCLOSURE

The invention relates to improvements in and relating to ophthalmoscopes particularly determining a correction for distortion in eye representations of ophthalmoscopes.

BACKGROUND

Ophthalmoscopes generally comprise a system for directing rays from a source onto a portion of a subject's eye and for collecting rays reflected from the portion of the subject's eye in a ray detector. A number of optical elements and scan elements are commonly used to direct and collect the rays, and the collected rays are used to form a representation of the portion of the subject's eye, often a portion of the retina of the subject's eye. Due to the three dimensional nature of the eye, the inherent characteristics of the optical elements and scan elements and customary operation modes used for such ophthalmoscopes, distortion can be introduced into the eye representations produced by the ophthalmoscopes. The distortion in the representations makes it difficult to determine accurately the size, structure and position of features of the portion of the subject's eye and to compare ophthalmoscope eye representations with eye representations taken using other devices. This can lead to difficulties in diagnosing and treating conditions of the eye.

SUMMARY

According to a first aspect of the invention there is provided a method of determining a correction for distortion in eye representations of an ophthalmoscope comprising
(i) constructing an optical description of a system comprising the ophthalmoscope and a model eye,
(ii) passing a ray through the system onto a surface of the model eye,
(iii) calculating an actual measurement of the ray at the surface,
(iv) determining a horizontal scanning angle and a vertical scanning angle of the system for the ray,
(v) calculating an expected measurement of the ray at the surface using the horizontal scanning angle and vertical scanning angle of the system,
(vi) repeating steps (ii) to (v) for a plurality of further rays, and
(vii) comparing the actual measurements of the rays at the surface with corresponding expected measurements of the rays at the surface to determine the correction for distortion in eye representations of the ophthalmoscope.

The rays that are passed through the system will be subjected to distortion of the ophthalmoscope and the eye, and the actual measurements of these rays at the surface of the eye will be 'with distortion' measurements. The expected measurements of the rays at the surface of the eye, which are calculated using the horizontal scanning angles and vertical scanning angles of the system, are 'without distortion' measurements. Hence a correction can be determined by comparing the actual and expected measurements.

The correction may be for geometric distortion in eye representations of the ophthalmoscope. The correction may be for angular geometric distortion in eye representations of the ophthalmoscope. The correction may be for spatial geometric distortion in eye representations of the ophthalmoscope. The correction may be for angular and spatial geometric distortion in eye representations of the ophthalmoscope.

Constructing an optical description of a system comprising the ophthalmoscope and the model eye may comprise determining optical path properties of the ophthalmoscope, determining optical path properties of the model eye and concatenating the optical path properties to give optical path properties of the system. Determining the optical path properties of the ophthalmoscope may comprise ascertaining components of the ophthalmoscope which have an optical path effect, ascertaining the order of the components in the ophthalmoscope, establishing a mathematical function describing the optical path properties over time of each component, concatenating in order the optical path properties of the components to give the optical path properties of the ophthalmoscope. Determining the optical path properties of the model eye may comprise ascertaining components of the model eye which have an optical path effect, ascertaining the order of the components in the model eye, establishing a mathematical function describing the optical path properties of each component, concatenating in order the optical path properties of the components to give the optical path properties of the model eye.

The surface of the model eye may be a retinal surface of the model eye.

Passing the rays through the system description onto the surface of the model eye may comprise using a ray tracing system. The ray tracing system may be a commercially available ray tracing system such as Zemax. Using the ray tracing system may comprise loading the optical description of the system into the ray tracing system and determining a path through the system for each of the rays.

Calculating the actual measurement of each ray at the surface may comprise calculating coordinates of a point of intersection of each ray with the surface.

Determining the horizontal scanning angle for a ray may comprise ascertaining an angular position of a horizontal scanning element of the ophthalmoscope used to produce the ray and using this to calculate the horizontal scanning angle for the ray. Determining the vertical scanning angle of the system for a ray may comprise ascertaining an angular position of a vertical scanning element of the ophthalmoscope used to produce the ray and using this to calculate the vertical scanning angle for the ray.

Calculating the expected measurement of each ray at the surface may comprise using the horizontal scanning angle and the vertical scanning angle of the system to calculate coordinates of a point of intersection of each ray with the surface.

Determining the correction for distortion in eye representations of the ophthalmoscope may comprise deriving an analytical transformation that maps the actual measurements of the rays at the surface of the model eye onto the corresponding expected measurements of the rays at the surface of the model eye. Determining the correction for distortion in eye representations of the ophthalmoscope may comprise constructing a correction look up table (LUT) comprising, for each of a plurality of rays, an actual location of the ray at the surface of the model eye against an expected location of the ray at the surface of the model eye.

The rays may comprise at least one ray for each of a plurality of pixels of eye representations of the ophthalmoscope. Calculating the actual measurements of the rays at the surface may comprise calculating coordinates of a point of intersection with the surface of at least one ray for each of the plurality of pixels. The at least one ray for each of the plurality of pixels may be a ray at a centre point of each pixel. Calculating the expected measurements of the rays at the surface may comprise using the horizontal scanning angle and the vertical scanning angle of the system to calculate coordinates of a point of intersection with the surface of at least one ray for each of the plurality of pixels.

The method may further comprise determining the correction for distortion in eye representations of the ophthalmoscope for a plurality of non-zero gaze angles of the model eye. For each non-zero gaze angle, this may further comprise measuring the gaze angle using a fovial location of the model eye. A correction LUT may be constructed for each of the plurality of non-zero gaze angles.

The ophthalmoscope of the system may be representative of a single, real ophthalmoscope or representative of a plurality of real ophthalmoscopes all having or purporting to have the same optical properties. The ophthalmoscope of the system may be representative of a proposed ophthalmoscope, for example an ophthalmoscope which is to be tested before its actual construction.

According to a second aspect of the invention there is provided a computer program which, when executed, performs the method of the first aspect of the invention. According to a third aspect of the invention there is provided a computer readable media storing program instructions which, when executed, perform the method of the first aspect of the invention.

According to a fourth aspect of the invention there is provided a method of correcting distortion in an eye representation acquired using an ophthalmoscope comprising obtaining a correction for distortion in eye representations of the ophthalmoscope using the method of the first aspect of the invention, and using the correction to map points of the acquired eye representation to corresponding points of a corrected eye representation.

The eye representation may comprise a retinal eye representation. Obtaining the correction for distortion in eye representations of the ophthalmoscope may comprise carrying out the method of the first aspect of the invention. Obtaining the correction for distortion in eye representations of the ophthalmoscope may comprise a third party carrying out the method of the first aspect of the invention and receiving the correction from the third party.

Using the correction may comprise using an analytical transformation to map points of the acquired eye representation to corresponding points of a corrected eye representation. Using the correction to map points of the acquired eye representation to corresponding points of a corrected eye representation may comprise using a correction LUT comprising a location of each of the points of the acquired eye representation against a location of the corresponding points of the corrected eye representation. Using the correction to map points of the acquired eye representation to corresponding points of a corrected eye representation may comprise using a correction LUT comprising, for a point of each of a plurality of pixels of the acquired eye representation, an identification of the pixel of the acquired eye representation against a location of the corresponding point of the corrected eye representation.

The method may further comprise measuring a gaze angle using a fovial location of the acquired eye representation, selecting a correction LUT for the gaze angle and using the selected correction LUT to map points of the acquired eye representation to corresponding points of a corrected eye representation.

The method may further comprise converting a 3D corrected eye representation to a 2D corrected eye representation using one of a known number of image projection techniques. The image projection technique may be a stereographic projection technique. The image projection technique may be a conformal projection technique, preserving angles from the 3D representation to the 2D representation. The image projection technique may be an equidistant projection technique, preserving distances from the 3D representation to the 2D representation. The image projection technique may be an area-preserving projection technique, preserving areas from the 3D representation to the 2D representation.

Converting the corrected eye representation from a 3D representation to a 2D representation may comprise interpolation of data of the 3D representation or interpolation of data of the 2D representation.

The 2D corrected eye representation may be used to calculate measurements of features of the eye. The measurements may comprise dimension, coordinates, arc-lengths, areas and angles of the features. The measurements of the features may be used for classification and longitudinal tracking of disease/trauma artefacts, to improve correlation between acquired eye representations, diagnostics and treatment planning. Meaningful comparison with other eye capture modalities is also possible, allowing correlated measurements of feature dimension, location etc. across multiple imaging modalities.

According to a fifth aspect of the invention there is provided a corrected eye representation obtained using the method of the fourth aspect of the invention. According to a sixth aspect of the invention there is provided a computer program which, when executed, performs the method of the fourth aspect of the invention.

According to a seventh aspect of the invention there is provided a computer readable media storing program instructions which, when executed, perform the method of the fourth aspect of the invention.

According to an eighth aspect of the invention there is provided an ophthalmoscope comprising a computer program according to the second aspect of the invention and/or a computer program according to the sixth aspect of the invention.

BRIEF DESCRIPTION OF DRAWINGS

Embodiments of the invention will now be described by way of example only with reference to the accompanying drawings, in which.

DETAILED DESCRIPTION

Figure 1:
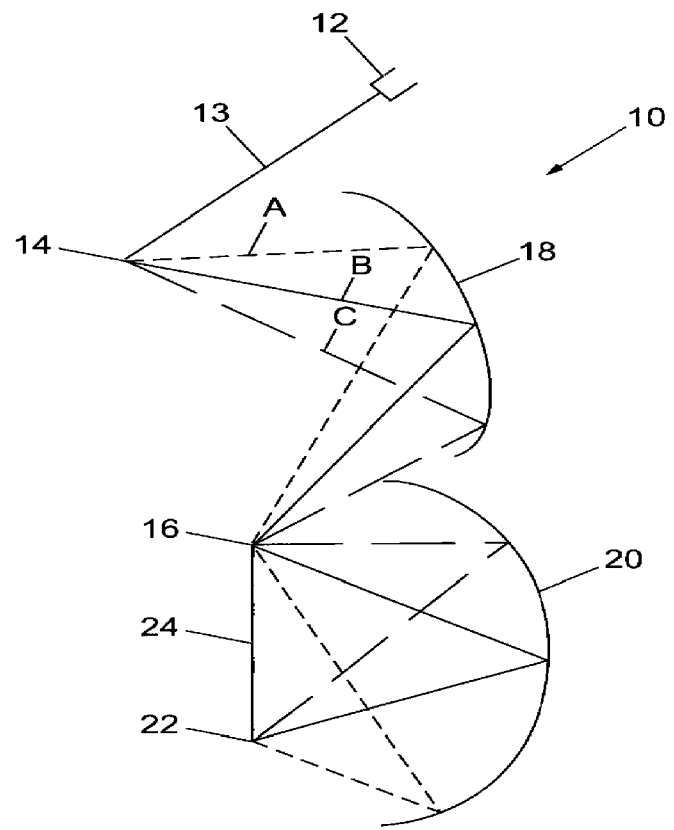
FIG. 1 is a schematic representation of an ophthalmoscope according to an embodiment of the invention.

Referring to FIG. 1, the ophthalmoscope 10 is an example of an ophthalmoscope which, when used to acquire representations of a patient's eye such as representations of a portion of the retina of the patient's eye, will introduce distortion into the acquired representations. The ophthalmoscope 10 comprises a source of collimated light 12, a first scanning element 14, a second scanning element 16, scan compensation means 18 and scan transfer means 20. The source of collimated light 12 directs a light beam 13 onto the first scanning element 14. This produces a scan of the beam (depicted by rays A, B and C) in a first, vertical, direction. The beam is incident on the scan compensation means 18 and is reflected from there onto the second scanning element 16. This produces a scan of the beam in a second, horizontal, direction. The beam is incident on the scan transfer means 20, which has two foci, the second scanning element 16 is provided at a first focus and an eye 22 of a patient is provided at the second focus. The beam from the second scanning element 16 which is incident on the scan transfer means 20 will be directed to the eye 22 and will impinge on a portion of the retina of the eye. The components of the ophthalmoscope 10 combine to provide a two dimensional scan of an incident beam from an apparent point source onto the retina portion. As the incident beam is scanned over the retina portion, it will be reflected therefrom to produce a reflected beam which is transmitted back through the components of the ophthalmoscope 10 and received by the one or more detectors (not shown).

To acquire a retinal representation, the incident beam is scanned over the retina portion of the eye 22 in a raster scan pattern, produced by the first and second scanning elements 14, 16 operating perpendicularly to each other. The first and second scanning elements are operated continuously to generate a continuous incident beam on, and a continuous reflected beam from, the retina portion from a scan start time to a scan stop time. The detectors are operated to record, or sample, the reflected beam over fixed time intervals of, for example, 30 ns throughout the scan. During each time interval, the incident beam is scanned over a part of the retina portion and the reflected beam from that part of the retina portion is recorded and assigned to a pixel associated with that part of the retina portion. The result is a pixelated representation of the retina portion.

In the ophthalmoscope 10 due to the inherent characteristics of the optical elements and scan elements 14, 16, 18 20 (and the three dimensional nature of the eye), the scan angle at the pupil plane is not uniform. In the customary operation mode of the ophthalmoscope 10, the angle covered in each, equal, time interval of the scan and the part of the retina portion scanned in each time interval is therefore non-linear with retinal arc length, resulting in distortion in acquired representations of the retina portion, which are comprised of non-uniform pixels. The pixels are not consistent in either angular or spatial extent introducing non-linearity or warping in the acquired representations of the retina portion when compared to the real retinal. The geometry of the acquired representations is determined by the time interval of sampling of the reflected beam and the angular scan pattern of the ophthalmoscope.

Figure 2:
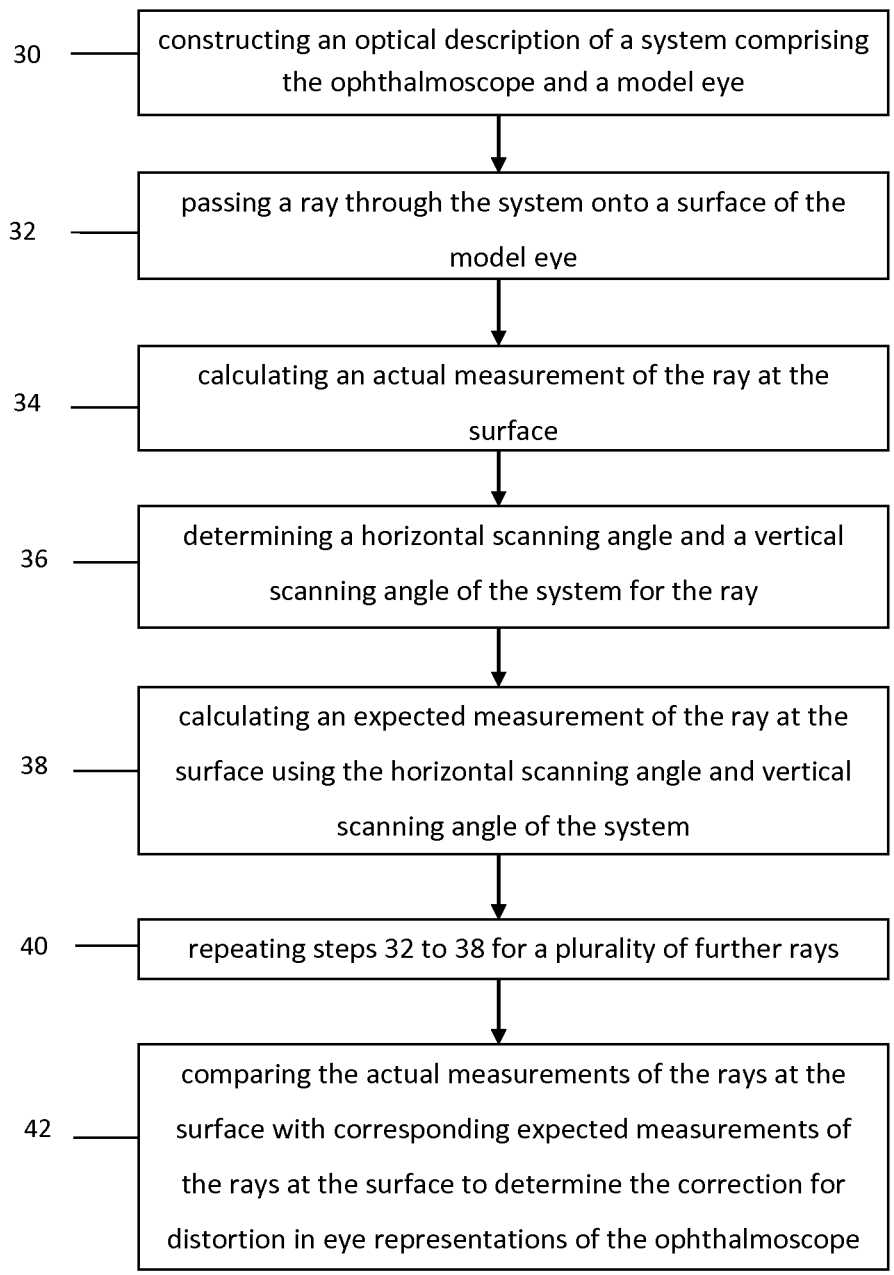
FIG. 2 is a flowchart representing the method of an aspect of the invention.

The ophthalmoscope 10 comprises a computer program (not shown) which, when executed, performs the method of determining a correction for distortion in retinal representations of the ophthalmoscope, and further comprises a computer program (not shown) which, when executed, performs the method of correcting distortion in retinal representations acquired using the ophthalmoscope. A correction for distortion in retinal representations of the ophthalmoscope 10 is determined as follows, FIG. 2. An optical description of a system comprising the ophthalmoscope 10 and a model eye is constructed (step 30). The model eye may be any of a number of standard model eyes. Optical path properties of the ophthalmoscope 10 and the model eye are determined and concatenated to give optical path properties of the system. The optical path properties of the ophthalmoscope 10 are determined by ascertaining components of the ophthalmoscope 10 which have an optical path effect, ascertaining the order of the components in the ophthalmoscope 10, establishing a mathematical function describing the optical path properties over time, of each component, and concatenating in order the optical path properties of the components to give the optical path properties of the ophthalmoscope 10. The optical path properties of the model eye may be known from information about the eye, or determined in a similar manner to the ophthalmoscope 10.

A ray is then passed through the optical description of the system onto a surface of the model eye (step 32), in this case the retinal surface of the model eye. This is achieved by loading the optical description of the system into Zemax ray tracing system and determining a path through the system for the ray. The ray is chosen such that it corresponds to a centre point of a pixel of acquired retinal representations of the ophthalmoscope 10. Ray-tracing takes into account all reflections and refractions etc. encountered along the entire optical path of the ophthalmoscope and the model eye and the scanning process of the ophthalmoscope.

An actual measurement of the ray at the retinal surface is then calculated (step 34) by calculating coordinates of a point of intersection of the ray with the retinal surface. The coordinates may be x, y coordinates or spherical coordinates at the retinal surface. A data file containing the intersection coordinates of the ray is produced by the Zemax ray tracing system.

A horizontal scanning angle and a vertical scanning angle of the system for the ray is then determined (step 36) by ascertaining an angular position of the horizontal scanning element 16 and an angular position of the vertical scanning element 14 of the ophthalmoscope 10 which would produce the ray and using these to calculate the scanning angles for the ray. An expected measurement of the ray at the retinal surface is calculated (step 38) using the horizontal scanning angle and the vertical scanning angle of the system to calculate coordinates of a point of intersection of the ray with the retinal surface.

The steps 32 to 38 are then repeated for a plurality of further rays (step 40). The rays are chosen such that they correspond to centre points of further pixels of acquired retinal representations of the ophthalmoscope 10.

The actual, or 'with distortion', measurements of the rays at the retinal surface are then compared with corresponding expected, or 'without distortion', measurements of the rays at the retinal surface to determine the correction for distortion in retinal representations of the optical description of the system and therefore of the ophthalmoscope 10 (step 42). Data files from the ray-tracing are analysed in Matlab to produce a correction comprising an analytical transformation that maps the actual measurements of the rays at the retinal surface onto the corresponding expected measurements of the rays at the retinal surface, and to construct a correction LUT comprising, for each of the pixels, an identification of the pixel against a location of the corresponding expected measurement of the ray of the pixel at the retinal surface.

Figure 3:
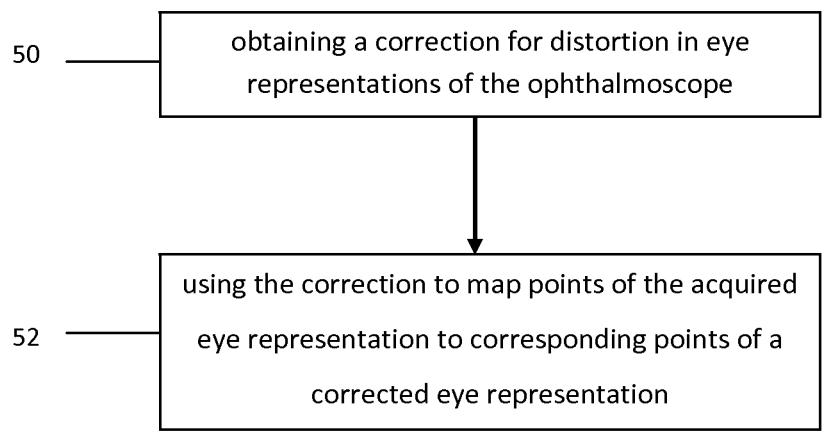
FIG. 3 is a flowchart representing the method of an aspect of the invention.

Retinal representations acquired using the ophthalmoscope 10 can then be corrected, FIG. 3. The correction to be used is obtained using the method described above (step 50). The correction is then used to map points of an acquired retinal representation to corresponding points of a corrected retinal representation (step 52). A correction LUT may be used to map the points of the acquired retinal representation to corresponding points of a corrected retinal representation.

The retinal representation correction method may further comprise measuring a gaze angle using a fovial location of the acquired retinal representation, selecting a correction LUT for the gaze angle and using the selected correction LUT to map points of the acquired retinal representation to corresponding points of a corrected retinal representation.

The retinal representation correction method may further comprise converting the a 3D corrected retinal representation to a 2D corrected representation using one of a known number of image projection techniques, for example a conformal stereographic projection technique. The stereographic projection maps coordinates of the corrected retinal representation onto a plane located at the centre of the eye and orthogonal to the optical axis. Mathematically, this projection transforms 3D Cartesian coordinates (x,y,z) of the corrected retinal representation onto 2D Cartesian coordinates (Y, Z), using the equations $$Y = \frac{yR}{R+x},$$
$$Z = \frac{zR}{R+x}$$

where R is the radius of the eye (typically R=12 mm). Some type of interpolation or pixel binning is necessary since the grid of the 3D spherical corrected retinal representation does not project unequivocally onto the square grid of the projection plane. Linear interpolation of the stereographically projected data is performed to produce the final retinal representation consisting of an equal number of horizontal and vertical pixels. The stereographic projection produces a more natural view of the retina by repositioning features to where they should be.

The 2D corrected retinal representation may be used to calculate measurements of features of the representation. The measurements may comprise dimension, coordinates, arc-lengths, areas and angles of the features. The measurements of the retinal features may be used for classification and longitudinal tracking of disease/trauma artefacts, to improve correlation between acquired retinal representations, diagnostics and treatment planning. Meaningful comparison with other retinal capture modalities is also possible, allowing correlated measurements of feature dimension, location etc. across multiple imaging modalities.

The correction method may further comprise using the correction LUT in a feedback loop to dynamically change the time interval of capture of pixel information of the acquired retinal representation.

What is claimed:

1. A method of determining a correction for distortion in eye representations of an ophthalmoscope comprising:
   (i) constructing a digital model of an optical system comprising the ophthalmoscope and a model eye,
   (ii) transmitting the digital model of the optical system to a ray tracing system and passing a ray through the optical system onto a surface of the model eye of the digital model,
   (iii) calculating a first measurement of the ray, with distortion, at the surface of the model eye,
   (iv) determining an angular position of a horizontal scanning element of the ophthalmoscope used to produce the ray and an angular position of a vertical scanning element of the ophthalmoscope used to produce the ray,
   (v) determining a horizontal scanning angle of the optical system and a vertical scanning angle of the optical system for the ray based on the angular position of the horizontal scanning element and the angular position of the vertical scanning element,
   (vi) calculating a second measurement of the ray at the surface of the model eye, without distortion, using the horizontal scanning angle of the optical system and the vertical scanning angle of the optical system, and
   (vii) comparing the first measurement, with distortion, of the ray at the surface of the model eye with the corresponding second measurement, without distortion, of the ray at the surface of the model eye to determine the correction for distortion in eye representations of the ophthalmoscope.

2. A method according to claim 1, in which constructing the optical system comprising the ophthalmoscope and the model eye comprises determining optical path properties of the ophthalmoscope, determining optical path properties of the model eye and concatenating the optical path properties to give optical path properties of the optical system.

3. A method according to claim 1, in which passing the ray through the optical system onto the surface of the model eye comprises using the ray tracing system and loading the optical system into the ray tracing system and determining a path through the system for the ray.

4. A method according to claim 1, in which calculating the first measurement of the ray at the surface comprises calculating coordinates of a point of intersection of the ray with the surface.

5. A method according to claim 1, in which calculating the second measurement of the ray at the surface comprises using the horizontal scanning angle and the vertical scanning angle of the system to calculate coordinates of a point of intersection of the ray with the surface.

6. A method according to claim 1, in which determining the correction for distortion in eye representations of the ophthalmoscope comprises deriving an analytical transformation that maps the first measurement of the ray at the surface of the model eye onto the corresponding second measurement of the ray at the surface of the model eye.

7. A method according to claim 1, in which determining the correction for distortion in eye representations of the ophthalmoscope comprises constructing a correction look up table (LUT) comprising an actual location of the ray at the surface of the model eye against a location of the corresponding expected location of the ray at the surface of the model eye.

8. A method according to claim 1, further comprising determining the correction for image distortion of the ophthalmoscope for a plurality of non-zero gaze angles of the model eye by further measuring the gaze angle using a fovial location of the model eye.

9. A method according to claim 8, in which a correction LUT is constructed for each of the plurality of non-zero gaze angles.

10. A computer readable non-transitory media storing program instructions which, when executed, perform a method of determining a correction for distortion in eye representations of an ophthalmoscope by:
   (i) constructing a digital model of an optical system comprising the ophthalmoscope and a model eye,
   (ii) transmitting the digital model of the optical system to a ray tracing system and passing a ray through the optical system onto a surface of the model eye of the digital model,
   (iii) calculating a first measurement, with distortion, of the ray at the surface of the model eye,
   (iv) determining an angular position of a horizontal scanning element of the ophthalmoscope used to produce the ray and an angular position of a vertical scanning element of the ophthalmoscope used to produce the ray, (v) determining a horizontal scanning angle of the optical system and a vertical scanning angle of the optical system for the ray based on the angular position of the horizontal scanning element and the angular position of the vertical scanning element, (vi) calculating a second measurement, without distortion, of the ray at the surface of the model eye using the horizontal scanning angle of the optical system and vertical scanning angle of the optical system, and (vii) comparing the first measurement, with distortion, of the ray at the surface of the model eye with the corresponding second measurement, without distortion, of the ray at the surface of the model eye to determine the correction for distortion in eye representations of the ophthalmoscope.

11. A method of correcting distortion in an eye representation acquired using an ophthalmoscope comprising:

obtaining a correction for distortion in eye representations of the ophthalmoscope by:

(i) constructing a digital model of an optical system comprising the ophthalmoscope and a model eye, (ii) transmitting the digital model of the optical system to a ray tracing system and passing a ray through the optical system onto a surface of the model eye of the digital model, (iii) calculating a first measurement, with distortion, of the ray at the surface of the model eye, (iv) determining an angular position of a horizontal scanning element of the ophthalmoscope used to produce the ray and an angular position of a vertical scanning element of the ophthalmoscope used to produce the ray, (v) determining a horizontal scanning angle of the optical system and a vertical scanning angle of the optical system for the ray based on the angular position of the horizontal scanning element and the angular position of the vertical scanning element, (vi) calculating a second measurement, without distortion, of the ray at the surface of the model eye using the horizontal scanning angle of the optical system and vertical scanning angle of the optical system, (vii) comparing the first measurement, with distortion, of the ray at the surface of the model eye with the corresponding second measurement, without distortion, of the ray at the surface of the model eye to determine the correction for distortion in eye representations of the ophthalmoscope; and using the correction to map points of the acquired eye representation to corresponding points of a corrected eye representation.

12. A method according to claim 11, further comprising measuring a gaze angle using a fovial location of the acquired eye representation, selecting a correction LUT for the gaze angle and using the selected correction LUT to map points of the acquired eye representation to corresponding points of a corrected eye representation.

13. A method according to claim 11, further comprising converting a corrected eye representation to a corrected eye representation using one of a known number of image projection techniques.

14. A method according to claim 11, in which the corrected eye representation is used to calculate measurements of features of the eye representation.

15. A method according to claim 11, further comprising obtaining a corrected eye representation.

16. A computer readable non-transitory media storing program instructions which, when executed, perform a method of correcting distortion in an eye representation acquired using an ophthalmoscope by:

obtaining a correction for distortion in eye representations of the ophthalmoscope by:

(i) constructing a digital model of an optical system comprising the ophthalmoscope and a model eye, (ii) transmitting the digital model of the optical system to a ray tracing system and passing a ray through the optical system onto a surface of the model eye of the digital model, (iii) calculating a first measurement, with distortion, of the ray at the surface of the model eye, (iv) determining an angular position of a horizontal scanning element of the ophthalmoscope used to produce the ray and an angular position of a vertical scanning element of the ophthalmoscope used to produce the ray, (v) determining a horizontal scanning angle of the optical system and a vertical scanning angle of the optical system for the ray based on the angular position of the horizontal scanning element and the angular position of the vertical scanning element, (vi) calculating a second measurement, without distortion, of the ray at the surface of the model eye using the horizontal scanning angle of the optical system and vertical scanning angle of the optical system, (vii) comparing the first measurement, with distortion, of the ray at the surface of the model eye with the corresponding second measurement, without distortion, of the ray at the surface of the model eye to determine the correction for distortion in eye representations of the ophthalmoscope; and using the correction to map points of the acquired eye representation to corresponding points of a corrected eye representation.

17. An ophthalmoscope comprising a computer readable non-transitory media storing program instructions which, when executed, perform a method of determining a correction for distortion in eye representations of an ophthalmoscope by:

(i) constructing a digital model of an optical system comprising the ophthalmoscope and a model eye, (ii) transmitting the digital model of the optical system to a ray tracing system and passing a ray through the optical system onto a surface of the model eye of the digital model, (iii) calculating a first measurement, with distortion, of the ray at the surface of the model eye, (iv) determining an angular position of a horizontal scanning element of the ophthalmoscope used to produce the ray and an angular position of a vertical scanning element of the ophthalmoscope used to produce the ray, (v) determining a horizontal scanning angle of the optical system and a vertical scanning angle of the optical system for the ray based on the angular position of the horizontal scanning element and the angular position of the vertical scanning element, (vi) calculating a second measurement, without distortion, of the ray at the surface of the model eye using the horizontal scanning angle of the optical system and vertical scanning angle of the optical system, (vii) comparing the first measurement, with distortion, of the ray at the surface of the model eye with the corresponding second measurement, without distortion, of the ray at the surface of the model eye to determine the correction for distortion in eye representations of the ophthalmoscope.

18. An ophthalmoscope comprising a computer readable non-transitory media storing program instructions which, when executed, perform a method of correcting distortion in an eye representation acquired using an ophthalmoscope by:
    obtaining a correction for distortion in eye representations of the ophthalmoscope by:
        (i) constructing a digital model of an optical system comprising the ophthalmoscope and a model eye,
        (ii) transmitting the digital model of the optical system to a ray tracing system and passing a ray through the optical system onto a surface of the model eye of the digital model,
        (iii) calculating a first measurement, with distortion, of the ray at the surface of the model eye,
        (iv) determining an angular position of a horizontal scanning element of the ophthalmoscope used to produce the ray and an angular position of a vertical scanning element of the ophthalmoscope used to produce the ray,
        (v) determining a horizontal scanning angle of the optical system and a vertical scanning angle of the optical system for the ray based on the angular position of the horizontal scanning element and the angular position of the vertical scanning element,
        (vi) calculating a second measurement, without distortion, of the ray at the surface of the model eye using the horizontal scanning angle of the optical system and vertical scanning angle of the optical system,
        (vii) comparing the first measurement, with distortion, of the ray at the surface of the model eye with the corresponding second measurement, without distortion, of the ray at the surface of the model eye to determine the correction for distortion in eye representations of the ophthalmoscope; and
    using the correction to map points of the acquired eye representation to corresponding points of a corrected eye representation.

\* \* \* \* \*